United States Patent
Farber et al.

(10) Patent No.: US 11,213,579 B2
(45) Date of Patent: Jan. 4, 2022

(54) VACCINES WITH ENHANCED IMMUNOGENICITY, LOW ALLERGENICITY AND REACTOGENICITY

(71) Applicants: Boris Farber, Brooklyn, NY (US); Sof'ya Farber, Brooklyn, NY (US); Artur Viktorovich Martynov, Kharkov (UA)

(72) Inventors: Boris Farber, Brooklyn, NY (US); Sof'ya Farber, Brooklyn, NY (US); Artur Viktorovich Martynov, Kharkov (UA)

(*) Notice: Subject to any disclaimer, the term of this patent is extended or adjusted under 35 U.S.C. 154(b) by 0 days.

(21) Appl. No.: 16/954,835

(22) PCT Filed: May 4, 2018

(86) PCT No.: PCT/RU2018/000291
§ 371 (c)(1),
(2) Date: Jun. 17, 2020

(87) PCT Pub. No.: WO2019/212378
PCT Pub. Date: Nov. 7, 2019

(65) Prior Publication Data
US 2021/0085774 A1 Mar. 25, 2021

(51) Int. Cl.
| | | |
|---|---|---|
| *A61K 39/104* | (2006.01) | |
| *A61K 39/17* | (2006.01) | |
| *A61K 39/39* | (2006.01) | |
| *A61K 39/00* | (2006.01) | |

(52) U.S. Cl.
CPC ............ *A61K 39/104* (2013.01); *A61K 39/17* (2013.01); *A61K 39/39* (2013.01); *A61K 2039/521* (2013.01); *A61K 2039/5252* (2013.01); *A61K 2039/55505* (2013.01)

(58) Field of Classification Search
CPC .......... A61P 35/00; A61P 31/12; A61P 37/04; A61P 31/20; A61P 37/02; C12N 2710/20022; C12N 7/00; C12N 2760/18134; A61K 38/4893; A61K 2039/6037; A61K 39/08; A61K 39/12; A61K 2039/6068; A61K 39/39; A61K 2039/525; A61K 2039/70; A61K 38/164; A61K 47/6415; A61K 2039/53; A61K 33/06; A61K 33/08; A61K 49/0056; A61K 9/5169; A61K 2039/5252; A61K 2039/55505; A61K 35/74; A61K 39/42; A61K 47/02; A61K 2039/521; A61K 41/00; A61K 41/17; C07K 14/005; C07K 2319/00; C07K 14/33; C07K 16/1282; C07K 14/195; G01N 2333/33; G01N 33/56911; A61B 5/14503

See application file for complete search history.

(56) References Cited

U.S. PATENT DOCUMENTS

| | | |
|---|---|---|
| 3,128,229 A | 4/1964 | b |
| 7,972,801 B2 * | 7/2011 | Atassi ..................... A61P 37/00 435/7.1 |
| 8,759,092 B2 | 6/2014 | Goodrich |

FOREIGN PATENT DOCUMENTS

| | | |
|---|---|---|
| EA | 025417 B1 | 12/2016 |
| RU | 2557968 C2 | 7/2015 |

OTHER PUBLICATIONS

Leibl et al. Vaccine , 1999, vol. 17, pp. 1017-1023.*
Mundt et al. Photochemistry and Photobiology, 2014, vol. 90, pp. 957-968.*

* cited by examiner

*Primary Examiner* — Bao Q Li
(74) *Attorney, Agent, or Firm* — Daniel M. Cohn; Howard M. Cohn

(57) ABSTRACT

Field of application: the invention relates to veterinary medicine and, in particular, to vaccinology and pharmacy, and is intended for the prevention and treatment of infectious and other diseases of humans and animals, where low allergenic low reactogenic vaccination is used. The essence of the invention: developed vaccines with increased immunogenicity, low allergenicity and reactogenicity, containing antigen/toxin and adjuvant, wherein that they contain vaccine antigen/toxin inactivated by electromagnetic radiation in the ultraviolet and visible regions of the spectrum in the presence of a solution of photosensitizer and salts of divalent metals, and then covalently modified according to the residues of amino groups and hydroxyls groups of antigen/toxin available for modification, at least two modifying agents at the same time in terms of 0.01-10.0% of the mass concentration of the antigen/toxin protein, and as an adjuvant it contains hydrosol hydroxide ferric chloride.

27 Claims, No Drawings

VACCINES WITH ENHANCED IMMUNOGENICITY, LOW ALLERGENICITY AND REACTOGENICITY

TECHNICAL FIELD

The invention relates to veterinary medicine and, in particular, to vaccinology and pharmacy and is intended for the prevention and treatment of infectious and other diseases of humans and animals where low allergenic low reactogenic vaccination is used.

PREVIOUS LEVEL OF TECHNOLOGY

In the modern world, vaccination is one of the main methods of preventing epidemics. There are two main groups of infectious diseases: a group of vaccine-controlled infections (the use of which prevents the epidemic), this groups are part of the mandatory vaccination regimen, and a second group of infections, against which vaccine prophylaxis mildly effective or totally ineffective [1].

The first group of infections includes conservative microorganisms and viruses whose antigenic composition is unchanged and the vaccine induces high levels of protective antibodies in the blood. These group are infections such as diphtheria, pertussis, measles, rubella, etc.

The second group of infectious diseases in which vaccination is mildly effective and mostly ineffective includes flu, herpes viruses, HIV/AIDS, and some others [2-4]. The ineffectiveness of vaccines in the prevention of this group of infections is due to a number of reasons. For example, an influenza virus is a polymorphic virus (a virus particle does not have a clear structure and shape) with a fragmented variable genome.

Influenza virus is very variable and capable of persistence (lifetime in the human body) [5]. In humans and animals (including birds [6]), this virus multiplies in several stages—in the acute productive phase, an infected cell releases virus particles that can infect neighboring cells [7]. In the persistence phase (latent phase), this virus "waits" inside the cell, while losing part of the fragmented genome or capturing pieces of human RNA in the cytoplasm [8]. According to statistics, the antigenic composition of the influenza virus per month changes by 5% [9].

Therefore, the use of standard approaches to the development of influenza vaccines is unpromising. Even the use of recombinant proteins and new types of gene vaccines does not save such drugs from rapid obsolescence. The presence of several conservative proteins in one ampoule (for example, hemagglutinins and neuraminidases for the influenza virus) does not protect the body from viral aggression by inducing the production of specific antibodies.

These antibodies will have a completely different monoclonal specificity, which will be necessary at this level of virus mutation. A change in the approach to designing vaccines should be accompanied by the inclusion of such antigens in the vaccines that have not yet appeared as a result of virus mutations [10]. The so-called predictive inclusion of antigens is possible in two ways: classic using the methods of epidemiological prediction of antigenic drift and by partially modifying antigens to obtain an unlimited number of antigen combinations in one antigen ampoule [11].

The first direction justified itself only partially: in no case did the prognosis of antigenic drift coincide with real mutational changes in neuraminidase and influenza hemagglutinin [12,13]. If we use the technology of partial modification of the protein component of the vaccine antigen, for example, type 1 neuraminidase, during the preparation of the vaccine, then content of one single dose of the vaccine, instead of one protein with one antigenic profile will have more than a million proteins with one primary and secondary structure, but different substitution sites and different antigenic profile.

The antibodies induced by this protein will block all possible combinations of attachment sites. Therefore, the number of induced monoclones will be an order of magnitude higher, although the amount of protein will remain the same. Moreover, any "future" epitope of the structure of neuraminidase will be blocked by already synthesized antibodies.

This approach allows: drastically reduce the dose of antigens used for vaccination, protect the body from viruses with a fragmented genome and highly variable microorganisms by a small dose of antibodies, but with a significantly larger spectrum of monoclonal specificity. Roughly speaking, the vaccine will contain a set of even those neuraminidase antigens that do not yet exist. In the blood previously vaccinated animals it will create the necessary pool of antibodies to the "future" strain of the virus. The use of such a vaccine will successfully protect the body from highly variable persistent, as well as low immunogenic viruses and microorganisms.

Inactivation of vaccine antigen is one of the main steps in vaccine production. Due to the formalin or propiolactone treatment of the vaccine antigen/toxin, the immunogenicity of the latter often drops by several orders of magnitude, and covalent modification of the proteins leads to abnormal allergenicity and reactogenicity due to the appearance of new immunogenic epitopes. One of the promising ways to eliminate the loss of immunogenicity and increased reactogenicity and allergenicity is to exclude covalent modification of the antigen modifier.

Such means include photodynamic inactivation of microorganisms. The essence of the method is to add initially non-toxic and completely harmless riboflavin to the suspension of the microorganism, followed by irradiation of the mixture with light of certain wavelengths. At the same time, riboflavin activation is observed, which in the presence of divalent metals exhibits nuclease activity—it irreversibly fragment's infectious RNA and DNA.

There is no covalent modification of proteins, riboflavin addition to it is observed, but only deamination and decarboxylation of a number of amino acids in the composition of protein antigens. This type modification practically does not affect the immunogenicity of the initial protein antigen, but inactivates toxins enzymatic receptor activity. Similar technology of toxin inactivation is widely used for blood sterilization in blood donation centers.

Although the spread of viral diseases such as HIV, HBV, HCV through blood transfusion is highly and efficiently controlled to a large extent, but still the threat of diseases from pathogenic microorganisms and bacterial contamination of platelet concentrates remains a serious threat with serious clinical consequences. Unlike well-formed strategies for inactivating pathogens for freshly frozen plasma using a solvent-detergent procedure or methylene blue and visible light, the development of a new technology for inactivating pathogens for cellular components of the blood, such as platelets and red blood cells, is still underway and requires more research in that direction [14].

The pathogen inactivation systems (PIS) have proven effective against numerous bacteria, viruses and parasites. Two main systems have been successfully used to disinfect platelet concentrates: treatment with psoralen and ultraviolet A (UV-A) and treatment with riboflavin (vitamin B2) and ultraviolet B (UV-B), both of which are directed to nucleic acids of pathogens. The ability of the Mirasol PRT system to neutralize both pathogens and white blood cells has previously been described.

The technology uses a combination of riboflavin and UV light to induce irreversible fragmentation of nucleic acids of pathogens and white blood cells (WBCs) to suppress the replication and function of pathogens (viruses, microorganisms, and fungi) [15]. So, PIS methods can be considered as a "paradigm shift" to ensure safe blood transfusion, since PIS uses various physical, chemical or photochemical methods to remove or inactivate cellular pathogens such as viruses, bacteria and parasites in blood components or their products without change immunogenicity of the latter.

These pathogen inactivation systems (PIS) methods include, but are not limited to, solvent/detergent (S/D), nanofiltration, and photochemical inactivation using methylene blue (MB), psoralen, or riboflavin. Currently, research on PIS technology for blood components (plasma and platelets) has made significant progress. Several inactivation methods can be selected, including MB, Psoralen, and Riboflavin. These methods target viral nucleic acids (NAs) through photochemical inactivation. Methylene blue (MB) is a phenothiazine dye that has a natural affinity for emergencies.

After exposure to visible light (620-670 nm), the MB can secrete reactive oxygen species (mainly singlet oxygen) using a photodynamic reaction to induce guanine-specific cleavage of viral RNA, which leads to irreversible inactivation of the virus. MB is effective in the inactivation of many capsular viruses. Although some allergic adverse reactions are sometimes reported, MB is used in 18 countries to inactivate single plasma containers with minimal toxicity, which confirms the long-term safety of MB-treated plasma [16].

Amotosalen (S-59), known as a strong photosensitizer, is a synthetic derivative of Psoralen, which previously isolated from numerous plants. Through three stages of light processing, mediated amotosalen also inhibits replication, the transcription mechanism, and the repair of nucleic acids. Psoralen-based plasma inactivation technology (Cerus, Concord, Calif.) has been introduced as a successful commercial Amotosalen/UVA product and has been used for almost ten years in more than 20 countries. This technology has been proven effective in the inactivation of a wide range of viruses, bacteria and parasites, as well as white blood cells contained in blood products, and are considered safe without any significant side effects or toxicity[17].

As a pathogen inactivator, riboflavin-based compounds (vitamin B2) work after exposure to ultraviolet radiation (265-370 nm). This photodynamic reaction generates singlet oxygen, which is responsible for the photooxidation of the guanine base of nucleic acids and leads to the breaking and fragmentation of the polynucleotide chain, which irreversibly damages nucleic acids (DNA or RNA) and deamination and decarboxylation of surface amino acids in proteins without a significant change in their structure and immunogenicity.

According to the FDA toxicity class, riboflavin is classified as "GRAS" (usually considered safe), due to its wide distribution in various natural foods and human blood, neither riboflavin nor its metabolic products need to be removed after processing. Many studies have shown the effectiveness of this technology in the inactivation of a wide range of pathogenic microorganisms (bacteria, viruses and protozoa, etc.). Mirasol (Terumo BCT, USA), based on Riboflavin/UVB PIS technology, has been used in many blood bank centers in many countries worldwide [18].

The benefits of PIS include: (a) PIS methods are primarily effective in preventing bacterial infections associated with transfusion; (B) PIS methods on a global scale reduce the risk of transmission of diseases through transfusion and replace γ-radiation for the prevention of GvHD. (B) Hemostatic efficacy of PIS, lasts for a long period of time. In a study by Castrillo et al. PIS according to the Mirasol method, demonstrated a minimal loss of platelet quality parameters. A minimal decrease in twisting was noted on the 7th day of storage, indicating that cell morphology is preserved in all cell populations.

In vitro studies have been shown that blood products (BPs) that were treated with PIS were widely reliably tested on a larger scale in the world and have significant wide documentation. The expression of the activated fibrinogen receptor, as it turned out, increases after PIS, most likely through the direct influence of PIS on this integrin. These data mainly related to the amostalen/UVA method and, to a lesser extent, to the riboflavin/UV method.

One of the most important criteria for ascertaining is the economic value and the possibility of wider application, especially in conditions of high requirements and limited resources, as is observed in developing countries. However, recent analyzes have shown that products that treat PRT can actually reduce the overall health care costs and length of hospital stay associated with post-transfusion care for some patients.

Due to the efficacy of the therapy, Mirasol PRT was able to inactivate all residual white blood cells in the product containing many viral antigens, it can be used as an alternative to γ-radiation, which can save medical expenses and further cost, and provides increased comfort of care to the patient. In addition, it was found that the Mirasol PRT system, which is considered the gold standard for the inactivation of residual white blood cells in blood products, prevents the accumulation and secretion of most WBC-associated cytokines with the potential for the prevention of leukocyte-mediated immunological reactions in patients [19].

The Mirasol system is easy to use and does not require special training for the equipment operation. This technology eliminates the residual risk for most bacteria, and also reduces the risk associated with a large list of transfusion pathogens which are not checked during blood transfusion. Additional studies are needed to fully understand the various mechanisms used for postinfusion infection (PI), and therefore PI remains a challenge in the near future, which in turn requires more concerted efforts to obtain long-term and stable clinical benefits.

But the above technologies were not used to replace formalin and merthiolate in vaccinology. The actual absence of allergic reactions to the products of processing microorganisms make this technology promising for use in vaccine production. A longer treatment of enzymes also led to their loss of catalytic properties [20], and blood treatment of patients with botulism riboflavin and UV radiation even led to inactivation of the toxin in the blood [21].

These prerequisites which gave us the idea of extrapolating the experience of transfusiologists with photodynamic inactivation of blood products to vaccinology in order to replace inactivators/preservatives with non-toxic metabolic photoinactivation agents that do not need to be purified from the vaccine and which do not form covalent bonds with vaccine antigens. Based on this information and facts it does not decrease in larger magnitude immunogenicity of the vaccines and it does not grossly increase their allergenicity and reactogenicity, mainly due to covalently altered antigen fragments with formalin.

Ensemble or Supramolecular Ensemble-Terms from Supramolecular Chemistry.

The objects of supramolecular chemistry are supramolecular ensembles built spontaneously from complementary, i.e., having geometrical and chemical correspondence of fragments, similar to spontaneous assembly of complex spatial structures in a living cell (Steed J. V., Atwood J. L. Supramolecular chemistry.—M.: Academic Book, 2007). Due to the fact that during the synthesis of one antigen molecule (or its fragment after proteolysis) in the presence of two modifiers, many derivatives are synthesized and between their molecules the intermolecular ionic and hydrogen bonds are formed.

Such supramolecular structures have a significantly higher biological activity than the original antigen—they form many chimeric molecules similar to the original antigen, but with the ability to induce the synthesis of thousands of different monoclones of immunoglobulins in the body. The experiment has confirmed that such supramolecular structure has the higher immunogenicity than that of an unmodified antigen. We used a combinatorial mixture of derivatives of pre-photoinactivated antigen in the form of a supramolecular ensemble without separation into separate components.

Simultaneous combinatorial modification with two modifiers—if a multifunctional molecule is used in the combinatorial synthesis reaction—in our case, a protein with antigenic properties or a polysaccharide with many groups available for simultaneous modification (amino groups, hydroxyl saccharide or amino acid groups), two modifying agents, for example, acetic anhydride and succinic anhydride, are immediately introduced into the reaction.

The reaction produces the antigens mixture of acylated in different positions—acetyl-succinyl derivatives. As a result, from a single molecule with five epitopes which inducing the synthesis of five monoclones of immunoglobulins in the body, induce hundreds of monoclonal immunoglobulins will be induced to hundreds of new epitopes.

There are well known vaccines with increased immunogenicity with partially modified antigens and altered charges of basic amino acids to the opposite charge [22]. The use of such vaccines can increase the efficiency of vaccination by increasing immunogenicity, expand the number of epitopes in their structure. The number of new epitopes is proportional to the number of derivatives in the supramolecular combinatorial mixture. These vaccines have several disadvantages: they do not show a decrease in reactogenicity and allergenicity against the initial antigen inactivated by formalin or by heating.

In addition, modification with a single modifier limits the number of derivatives and epitopes and limits their immunogenicity. Our invention includes vaccines that contain not only non-covalently inactivated antigen without loss of immunogenicity, but also due to two modifiers are two orders of magnitude more immunogenic due to an increase in the number of derivatives of antigenic determinants.

DISCLOSURE OF INVENTION

The objective of the invention is to develop vaccines with increased immunogenicity, low allergenicity and reactogenicity.

The problem is solved by obtaining vaccines with increased immunogenicity, low allergenicity and reactogenicity, containing antigen/toxin and adjuvant, characterized in that the vaccines contain the original antigen/toxin first inactivated by electromagnetic radiation in the ultraviolet and visible spectral regions in the presence of a solution of photosensitizer and salts of divalent metals, and then covalently modified at accessible for modification residues of the amino groups and hydroxyl groups of the antigen/toxin at least umya modifying agents 0.01-10.0% based on the mass concentration of the antigen protein/toxin as adjuvant and comprises ferric hydroxide hydrosol.

As a photosensitizer can be used including, but not limited to: riboflavin, riboflavin mononucleotide, riboflavin dinucleotide, methylene blue, toluidine blue, dimethylmethylene blue, chlorophylls, hemporphyrins, cobolamines or a mixture of them. The following can be used as antigens: living microorganism corpuscles, microorganism phagolysate, virions, microbial exotoxin, microbial endotoxin, mixture of acellular microbial antigens, microbial glycoprotein, microbial glycoprotein mixture, microbial peptide, microbial peptide mixture, microbial polysaccharides, a mixture of microbial lipopolysaccharides, a whole virion, a viral protein, a mixture of viral proteins.

Moreover, these antigens can be pre-cut with proteolytic enzymes including, but not limited to: trypsin, pepsin, proteinase-K, chymotrypsin, or using synthetic proteases. Water-soluble salts, inclusively, but not excluding magnesium, calcium, zinc, iron, copper, strontium, cobalt, nickel, can be used as bivalent metals—enhancers of photocatalysis/photonucleolysis, either separately or in mixtures with each other.

For covalent modification of lysine and histidine residues of the protein component of the antigen/toxin, acylation is used including, but not limited to anhydrides of carboxylic and polycarboxylic acids, alkylation including, but not limited to halogenated carboxylic and polycarboxylic acids, or both acylation and alkylation including, but not limited to, anhydrides acids and halogen derivatives of carboxylic and polycarboxylic acids, respectively.

The described application can be used in the development of vaccines for the prevention of infections such as influenza, hepatitis, herpes viruses, measles, rubella, HIV/AIDS, animal viral infections: Newcastle disease, infectious bursal disease of the bird, classical swine fever, African swine fever and any other diseases, the treatment of multiple sclerosis.

Due to the partial modification of the structure during the modification reaction, a huge number of various vaccine antigen derivatives with different immunogenicity and structure are formed, and accordingly, the immune system induces the synthesis of more monoclones in response to these new antigenic determinants. In addition, such variety of new epitopes (hundreds of thousands or even millions) allows us to predictively protect the body from future nonexistent strains of the flu and mutant HIV/AIDS viruses.

The vaccines can be used for parenteral administration (subcutaneously, intradermally, intramuscularly and intravenously); oral administration in the form of tablets, capsules, sublingual tablets, candies for children, ice cream, sweets like candies, lozenges, sublingual strip, drinks; rectal administration in the form of suppositories; transdermal administration in the form of transdermal ointments, gels, patches or devices; intranasal administration in the form of nebulizer devices via aerosol, spraying or in the form of intranasal drops or ointments.

The immunogenicity of protease-fragmented vaccines is ensured by the formation of chimeric supramolecular structures similar to the parent proteins, but in a wide variety of forms.

THE BEST EMBODIMENT OF THE INVENTION

Example 1—Obtaining a Corpuscular Vaccine

Inactivation of bacteria by the example of *Pseudomonas aeruginosa* using the method of photodynamic inactivation.

*Pseudomonas aeruginosa* was cultured on solid nutrient medium (Mueller-Hinton medium (MHA) with the addition of 1% glucose). Three days later, the surface of the nutrient medium was completely covered with *P. aeruginosa* 6616 (Ukraine, Kharkov, IMI). To receive the vaccine, it is planned to develop a vaccine. From the surface of the medium in a Petri dish washings were made with a 0.9% sodium chloride solution, and the suspension as result of washing was washed out again three times and centrifuged.

After repeated process of suspension, riboflavin (or riboflavin mononucleotide, riboflavin dinucleotide, methylene blue, toluidine blue, dimethylmethylene blue) was added to a final concentration of 5-640 nM, then left for 2-40 min, 1-1000 mmol/l of divalent metal salt solution was added (as salts of divalent metals, water-soluble salts can be used both separately and in mixtures with each other, inclusive, but not excluding: magnesium, calcium, zinc, iron, copper, strontium, cobalt, nickel) as an activator of nucleolysis. It was treated with electromagnetic radiation in the ultraviolet or visible region of the optical spectrum for 2-50 minutes at a power of 10-900 μV/ml, and then again seeded on MHA in order to control inactivation.

Table 1 presents the results of the dependence of the inactivation efficiency on the inactivator and its dose when irradiated for 5 minutes with light with a wavelength of 320 nm and a power of 500 μV/ml for flavins and at 560 nm for phenothiazines and porphyrins.

Table 2 shows the results of the dependence of the inactivation efficiency on the wavelength of electromagnetic radiation at an emitter power of 500 μV/ml, a processing time of 5 minutes, and a concentration of each photoinactivator of 40 μM/L using a white LED lamp and a prism to isolate the desired wavelengths.

TABLE 1

The dependence of the effectiveness of inactivation of *P. aeruginosa* on the inactivator and its dose at an initial dose of 10 lg CFU/ml

| No. p/p | Photosensitizer | Concentration nM/L | lg CFU/ml after treatment |
|---|---|---|---|
| 1. | Riboflavin | 1 | 6 |
| 2. | | 5 | 2 |
| 3. | | 10 | 1 |
| 4. | | 20 | 0 |
| 5. | | 40 | 0 |
| 6. | | 80 | 0 |
| 7. | | 160 | 0 |
| 8. | | 320 | 0 |
| 9. | | 640 | 0 |
| 10. | | 1280 | -* |
| 11. | Riboflavin mononucleotide | 1 | 4 |
| 12. | | 5 | 1 |
| 13. | | 10 | 0 |
| 14. | | 20 | 0 |
| 15. | | 40 | 0 |
| 16. | | 80 | 0 |
| 17. | | 160 | 0 |
| 18. | | 320 | 0 |
| 19. | | 640 | 0 |
| 20. | | 1280 | -* |
| 21. | Riboflavin dinucleotide | 1 | 3 |
| 22. | | 5 | 0 |
| 23. | | 10 | 0 |
| 24. | | 20 | 0 |
| 25. | | 40 | 0 |
| 26. | | 80 | 0 |
| 27. | | 160 | 0 |
| 28. | | 320 | 0 |
| 29. | | 640 | 0 |
| 30. | | 1280 | -* |
| 31. | Methylene blue | 1 | 6 |
| 32. | | 5 | 2 |
| 33. | | 10 | 1 |
| 34. | | 20 | 1 |
| 35. | | 40 | 0 |
| 36. | | 80 | 0 |
| 37. | | 160 | 0 |
| 38. | | 320 | 0 |
| 39. | | 640 | 0 |
| 40. | | 1280 | 2 |
| 41. | Toluidine Blue | 1 | 6 |
| 42. | | 5 | 2 |
| 43. | | 10 | 1 |
| 44. | | 20 | 1 |
| 45. | | 40 | 0 |
| 46. | | 80 | 0 |
| 47. | | 160 | 0 |
| 48. | | 320 | 0 |
| 49. | | 640 | 0 |
| 50. | | 1280 | 2 |
| 51. | Dimethylmethylene blue | 1 | 2 |
| 52. | | 5 | 1 |
| 53. | | 10 | 1 |
| 54. | | 20 | 1 |
| 55. | | 40 | 0 |
| 56. | | 80 | 0 |
| 57. | | 160 | 0 |
| 58. | | 320 | 0 |
| 59. | | 640 | 0 |
| 60. | | 1280 | 1 |
| 61. | Chlorophyll alpha (on TWEEN-80) | 1 | 2 |
| 62. | | 5 | 2 |
| 63. | | 10 | 1 |
| 64. | | 20 | 1 |
| 65. | | 40 | 0 |
| 66. | | 80 | 0 |
| 67. | | 160 | 0 |
| 68. | | 320 | 0 |
| 69. | | 640 | 0 |
| 70. | | 1280 | -* |
| 71. | Heme | 1 | 3 |
| 72. | | 5 | 2 |
| 73. | | 10 | 2 |
| 74. | | 20 | 1 |
| 75. | | 40 | 0 |
| 76. | | 80 | 0 |
| 77. | | 160 | 0 |
| 78. | | 320 | 0 |
| 79. | | 640 | 0 |
| 80. | | 1280 | -* |
| 81. | Cyanocobalamin | 1 | 6 |
| 82. | | 5 | 5 |
| 83. | | 10 | 4 |
| 84. | | 20 | 4 |
| 85. | | 40 | 4 |
| 86. | | 80 | 2 |
| 87. | | 160 | 3 |
| 88. | | 320 | 2 |
| 89. | | 640 | 0 |
| 90. | | 1280 | -* |

*- not tested due to the inability to achieve the target concentration

As can be seen from table 1, in the range of concentrations from 5 to 640 nM/L, most photoinactivators showed sufficient efficiency to inactivate *Pseudomonas aeruginosa*.

The following microbial vaccine antigens can also be used as initial microbial phagolysates, microbial exotoxin, microbial endotoxin, acellular microbial antigens, microbial glycoprotein, microbial glycoprotein mixture, microbial peptide, microbial peptide mixture, microbial polysaccharide, microbial polysaccharide, microbial polysaccharide, lipopolysaccharides.

Before or after photoinactivation, such antigen/toxin can be cut into fragments using proteases, including but not limited to trypsin, pepsin, proteinase-K, chymotrypsin, using synthetic proteases. As salts of divalent metals, water-soluble salts can be used both separately and in mixtures with each other, inclusive, but not excluding: magnesium, calcium, zinc, iron, copper, strontium, cobalt, nickel.

Instead of the bacterial antigen/toxin from the variations described above, a whole virion, a viral protein, a mixture of viral proteins or pre-cut protease viral antigens can be used. Viruses: influenza, hepatitis, herpes viruses, measles, rubella, HIV/AIDS, animal viral infections: Newcastle disease, infectious bursal disease of the bird, classical swine fever, African swine fever and any other diseases can be used as initial antigens, multiple sclerosis therapy.

Due to the partial modification of the structure during the modification reaction, a huge number of various vaccine antigen derivatives with different immunogenicity and structure are formed and, accordingly, the immune system induces the synthesis of more monoclones in response to these new antigenic determinants. In addition, such a variety of new epitopes (hundreds of thousands or even millions) allows us to predictively protect the body from future nonexistent strains of the flu and mutant HIV/AIDS viruses.

TABLE 2

The dependence of the efficiency of inactivation of *P. aeruginosa* depending on the wavelength of electromagnetic radiation at an initial dose of 10 lg CFU/ml

| № p/p | Photosensitizer | Wavelength nm | lg CFU/ml after treatment |
|---|---|---|---|
| 1. | Riboflavin | 180 | 0 |
| 2. | | 220 | 2 |
| 3. | | 260 | 1 |
| 4. | | 320 | 0 |
| 5. | | 360 | 0 |
| 6. | | 400 | 0 |
| 7. | | 440 | 0 |
| 8. | | 480 | 0 |
| 9. | | 520 | 9 |
| 10. | | 560 | 8 |
| 11. | | 600 | 9 |
| 12. | | 640 | 9 |
| 13. | | 680 | 7 |
| 14. | | 720 | 6 |
| 15. | Methylene blue | 180 | 10 |
| 16. | | 220 | 9 |
| 17. | | 260 | 8 |
| 18. | | 320 | 9 |
| 19. | | 360 | 9 |
| 20. | | 400 | 9 |
| 21. | | 440 | 9 |
| 22. | | 480 | 7 |
| 23. | | 520 | 4 |
| 24. | | 560 | 3 |
| 25. | | 600 | 3 |
| 26. | | 640 | 0 |
| 27. | | 680 | 0 |
| 28. | | 720 | 0 |
| 29. | Chlorophyll alpha | 180 | 9 |
| 30. | (on TWEEN-80) | 220 | 9 |
| 31. | | 260 | 10 |
| 32. | | 320 | 10 |
| 33. | | 360 | 10 |

TABLE 2-continued

The dependence of the efficiency of inactivation of *P. aeruginosa* depending on the wavelength of electromagnetic radiation at an initial dose of 10 lg CFU/ml

| № p/p | Photosensitizer | Wavelength nm | lg CFU/ml after treatment |
|---|---|---|---|
| 34. | | 400 | 9 |
| 35. | | 440 | 9 |
| 36. | | 480 | 6 |
| 37. | | 520 | 7 |
| 38. | | 560 | 0 |
| 39. | | 600 | 0 |
| 40. | | 640 | 4 |
| 41. | | 680 | 6 |
| 42. | | 720 | 9 |

Double Covalent Modification of the Particle Antigen to Increase Vaccine Immunogenicity According to the number of microbial bodies, the resulting suspension was containing 10 billion cells/ml or 10 lg CFU/ml; then 0.1 ml of the suspension was diluted 100 times with 0.9% sodium chloride solution and the surface protein concentration was determined using the Biuret method or in the complexation reaction with the bromphenol blue method of Flores or spectrophotometrically using the Kalkar formula.

In terms of protein, a double covalent modification reaction was carried out by adding to the suspension of inactivated bacteria crushed to succinic and maleic anhydride powder in an amount of from 0.01 to 10% of the specified amount of protein. Instead of succinic and maleic anhydrides, other combinations of modifiers can be used including, but not limited to: anhydrides of carboxylic and polycarboxylic acids, halides of carboxylic and polycarboxylic acids. When using less than 0.01% degree of acylation, the immunogenicity of the vaccine does not differ from the immunogenicity of the unmodified antigen. When using degrees of modification of more than 10%, the immunogenicity of the vaccine drops to values less than that of the original unmodified antigen.

As a result of the modification reaction, 8 samples with different degrees of acylation were obtained: 1%, 3%, 5%, 7%, 9%, 11%, 13%, 15%. Exceeding 15% completely deprives immunogenicity of modified antigens, therefore derivatives with degrees of modification greater than 15% were not considered advisable to receive and use in the future. Corpuscular antigen with varying degrees of modification was further used to establish its immunogenicity.

The other part of the antigen was centrifuged for 40 minutes at 3 thousand rpm. The precipitate was discarded, and the supernatant was passed through a Sephadex G-75 column. The first, heaviest fraction was collected and used further to establish the protein concentration and degree of chemical modification. The resulting antigen was a homogeneous fraction (one polymer substance) and had a molecular weight of 1.5 mDa and a charge of −186000. Received a soluble glycoprotein antigen with such degrees of modification: 1%, 3%, 5%, 7%, 9%, 11%, 13%, 15%.

Polysaccharide antigen was also obtained from inactivated bacterial corpuscles. A suspension of inactivated bacteria was boiled for 40 minutes, centrifuged for 30 minutes at 10 g, the supernatant with polysaccharides was separated. Polysaccharides were precipitated from the supernatant by adding twice the volume of ethanol. The polysaccharide precipitate was separated by centrifugation, then dried. Modification was carried out after the polysaccharides were dissolved in distilled water in terms of polysaccharides (the number of polysaccharides was determined gravimetrically) with the following degrees of modification: 1%, 3%, 5%, 7%, 9%, 11%, 13%, 15%. The amount of each modifier was added in ½ dose from the calculated in the same proportion.

Antigens can be modified, but not limited to alkylation, acylation with modifiers such as carboxylic and polycarboxylic acid anhydrides, halogenated carboxylic and polycarboxylic acids, either individually or in a different combination or mixture.

As an adjuvant, 0.02-15% iron hydroxide hydrosol of the vaccine volume was used.

It is well known that when using gel filtration, the distribution of proteins passes over the size of the protein globule. Gel filtration was performed on columns filled with Sephadex G-75 gel. The total volume of the gel column was determined by Vt. During elution, large molecules that do not penetrate into the granules of the gel move with high speed together with the intergranular solvent and appear as a narrow strip. The volume of the eluent, which corresponds to the appearance of this zone, was determined as V0 (free volume).

Smaller molecules passed the column slowly, penetrated into the granules of the gel, and their exit from the column was very long lasting. Due to the fact that the degree of diffusion into the granules of the gel depends on the size of the molecules, the substances are released from the column in order as size of molecular weight was decreasing. The molecular mass M of the experimental protein was determined by comparing the elution volume Ve with a similar parameter of marker proteins.

A column with a diameter of 25 mm and a length of 1000 mm was used to isolate the antigen. Gel Sephadex G-75 and G-25 were preliminarily prepared in such a way: gel granules were slowly added to the buffer solution (0.1 M TRIS-HCl and 0.1 M NaCl, pH=8.0), kept in the thermostat for 72 hours at t=37 0 C. Then the gel was diaererised (gradually and carefully mixed in excess buffer solution to remove gas bubbles) on a shaker for an hour.

Filter paper was placed at the bottom of the column A little buffer solution was slowly added to the column, then a small amount (5 g) of a suspension of swollen Sephadex G-25 gel pellets was transferred along the wall. After the gel column was formed, at least two volumes of the working buffer solution were passed through the column. Then, 100 μl of the sample solution was micropipeted. A constant elution rate was set due to the establishment of a dropper with a buffer solution over the column, and the elution rate was controlled by a roller. The eluate was collected in 0.5 ml tubes and analyzed on an SF-56 spectrophotometer at a wavelength of 280 nm.

Anti-*Pseudomonas* serum for diagnostic purposes with a titer of specific anti-*Pseudomonas* antibodies (1:1000) was obtained according to the standard scheme for immunizing rabbits by introducing corpuscular inactivated antigen in Freund's adjuvant, according to the standard scheme 3; 5 and 7 days at a dose of 0.2 ml intramuscularly.

For immunization of animals, modified samples of both corpuscular antigen (CA) and modified soluble glycoprotein antigen (GA), polysaccharide antigen (PA) were tested. Also, a phagolysate antigen was prepared similarly to a corpuscular antigen: for 3 hours, 0.1 ml of pyobacteriophage (Russia, Ufa) was added to a suspension of 10 lg CFU/ml. Furthermore, inactivation was performed by riboflavin under standard conditions specified in paragraphs. in the presence of divalent metal cations. Antigen inactivation. The inactivated corpuscular phagolysate antigen was also modified with two modifiers to form a covalently modified corpuscular phagolysate antigen.

The level of antibodies was established by two methods: a hemagglutination reaction and a method of fluorescent antibodies. The three animals from each group were left alive for up to 15 days, then decapitated with chloroform and serum was obtained, where the level of specific antibodies was also established by the above methods.

To implement this, a test system for the direct hemagglutination reaction was prepared, which was carried out in 96-well round-bottom immunological plates, to which 0.02 ml of a 0.1% suspension of thermostated ram red blood cells and 0.02 ml of a suspension of thermally inactivated *Pseudomonas aeruginosa* cells were added at a concentration 10 billion cells/ml. Antibody levels were determined by serial ten-fold (but two-fold) dilutions of the mice serum, which were added in an amount of 0.02 ml to the wells of the plates. The presence of agglutinates testified to the formation of immune complexes. As controls, we used normal human immunoglobulin (anti-*Pseudomonas* antibody titer ranged from 0 to (1:10) according to the AED) and the blood serum of unvaccinated mice (titer from 0 to 1:10).

The obtained modified antigen can be sorbed by standard methods known to an ordinary person skilled in the art on an iron hydroxide hydrosol to further prolong the effects of the vaccine. A hydrosol is obtained by boiling a 0.1-20% solution of ferric chloride in water, followed by rapid cooling of the solution. Rapid cooling of the solution makes it possible to obtain nanosized nuclei of an iron hydrosol of hydroxide hydrochloride as colloidal particles. Such particles have the ability to significantly stimulate cellular immunity through siderophore receptors, as well as prolong the contact of vaccine antigens with plasma cells and other lymphocytes. Unlike the classic aluminum hydroxide adjuvant, the iron hydroxide hydrosol is completely metabolized and harmless to the human body.

The results of the studies of the immunogunity of vaccine antigen samples using the example of *Pseudomonas aeruginosa* sorbed on nanoparticles of hydrosol of iron hydroxide hydrochloride are shown in Table 3.

TABLE 3

The dependence of the immunogenicity of binary covalently modified antigens on the degree of modification using different antigens of *Pseudomonas aeruginosa* as an example

| № p/p | Antigen | The degree of modification, % | Induced titer of neutralizing antibodies (1:X), X * |
|---|---|---|---|
| 43. | CA | 1 | 520 |
| 44. | | 3 | 7000 |
| 45. | | 5 | 14000 |
| 46. | | 7 | 7000 |
| 47. | | 9 | 150 |
| 48. | | 11 | 75 |
| 49. | | 13 | 75 |
| 50. | | 15 | 25 |
| 51. | GA | 1 | 520 |
| 52. | | 3 | 14000 |
| 53. | | 5 | 14000 |
| 54. | | 7 | 14000 |
| 55. | | 9 | 150 |
| 56. | | 11 | 75 |
| 57. | | 13 | 75 |
| 58. | | 15 | 25 |
| 59. | PA | 1 | 20 |
| 60. | | 3 | 150 |
| 61. | | 5 | 150 |
| 62. | | 7 | 150 |
| 63. | | 9 | 150 |

TABLE 3-continued The dependence of the immunogenicity of binary covalently modified antigens on the degree of modification using different antigens of *Pseudomonas aeruginosa* as an example

| № p/p | Antigen | The degree of modification, % | Induced titer of neutralizing antibodies (1:X), X * |
|---|---|---|---|
| 64. |    | 11 | 75 |
| 65. |    | 13 | 75 |
| 66. |    | 15 | 25 |
| 67. | CF | 1  | 520 |
| 68. |    | 3  | 28000 |
| 69. |    | 5  | 28000 |
| 70. |    | 7  | 14000 |
| 71. |    | 9  | 5000 |
| 72. |    | 11 | 2500 |
| 73. |    | 13 | 1250 |
| 74. |    | 15 | 520 |

$P < 0.05$; * - differences from control are statistically significant

As per table 3, the largest titers of antibodies induced by phagolysate-corpuscular covalently modified antigen. At degrees of modification from 3 to 7, the titer exceeded the original native (1:20 for unmodified antigens except the polysaccharide, for which the titer was 1:10). Therefore, the advantage of our invention is that the bivalent modification after inactivation by the photodynamic method allows to increase the immunogenicity of antigens by several orders of magnitude based on the neutralization of unmodified corpuscles. In the prototype, it was possible to increase the immunogenicity of the antigen only to a titer of 1:5000.

Determination of Reactogenicity and Allergenicity of Vaccines

Studies of the reactogenicity and allergenicity of the solution of each of the vaccine antigens were carried out on healthy guinea pigs weighing 300-400 g of 3 animals in each the control and experimental groups. In experimental animals, fur was depilated on the sides. To determine the reactogenicity, a solution of the corresponding antigen was injected intracutaneously on one side of the body in a volume of 0.2 ml.

To determine allergenicity, test animals were injected intracutaneously with a triple vaccine antigen in a volume of 0.2 ml with an interval of 14 days, and 14 days after the last injection, guinea pigs were injected with a subcutaneous vaccine antigen in a volume of 0.2 ml.

The animals of the control group were injected with saline. The place of administration of the vaccine antigen was monitored for the occurrence of local reactions in the first 5 minutes and every 2 hours for 24 hours. Redness of the skin at the injection site in the area of not more than 5 mm is allowed.

As a result of the studies, it was found that none of the modified antigens with degrees of modification from 3 to 15% showed reactogenicity and allergenicity. Among the unmodified antigens, the glycoprotein soluble antigen showed reactogenicity, and the phagolysate unmodified antigen showed allergen after repeated administrations.

Example 2—the Obtaining Vaccine Based on Viral Virion of Newcastle

Newcastle Disease Virus Inactivation

The fluid culture containing 10 lg TCA50/ml of Newcastle disease virus (strain 2M—Kiev) obtained by well-known specialists in this field by the standard method of cultivating the virus on chicken embryos, add riboflavin (or riboflavin mononucleotide, riboflavin dinucleotide, methylene blue, toluidine blue, dimethylmethylene blue) to a final concentration of 5-640 nM, left for 2-40 minutes, 1-1000 mM/l solution of a divalent metal salt was added (as salts of divalent metals they can be used as In just the same way, in a mixture with each other, water-soluble salts, inclusive, but not excluding: magnesium, calcium, zinc, iron, copper, strontium, cobalt, nickel) as a nucleolysis activator, were treated with electromagnetic radiation in the optical spectral region 180-700 nm for 2-50 minutes at a power of 10-900 µV/ml, and then introduced into the chicken fibroblast culture to control inactivation according to the degree of culture degradation—cytopathic effect.

Table 4 presents the results of the dependence of the inactivation efficiency on the inactivator and its dose when irradiated for 5 minutes with light with a wavelength of 320 nm and a power of 500 µV/ml for flavins and at 560 nm for phenothiazines and porphyrins.

Table 4 shows the results of the dependence of the inactivation efficiency on the wavelength of electromagnetic radiation at an emitter power of 500 µV/ml, a processing time of 5 minutes, and a concentration of each photoinactivator of 40 µM/L using a white LED lamp and a prism to isolate the desired wavelengths.

TABLE 4

The dependence of the effectiveness of the inactivation of the Newcastle disease virus with an initial dose of 10 lg TCA50/ml

| № p/p | Photosensitizer | Concentration nM/L | lg TCA50/ml after treatment |
|---|---|---|---|
| 91. | Riboflavin | 1 | 7 |
| 92. |  | 5 | 1 |
| 93. |  | 10 | 0 |
| 94. |  | 20 | 0 |
| 95. |  | 40 | 0 |
| 96. |  | 80 | 0 |
| 97. |  | 160 | 0 |
| 98. |  | 320 | 0 |
| 99. |  | 640 | 0 |
| 100 |  | 1280 | -* |
| 101 | Riboflavin | 1 | 3 |
| 102 | mononucleotide | 5 | 0 |
| 103 |  | 10 | 0 |
| 104 |  | 20 | 0 |
| 105 |  | 40 | 0 |
| 106 |  | 80 | 0 |
| 107 |  | 160 | 0 |
| 108 |  | 320 | 0 |
| 109 |  | 640 | 0 |
| 110 |  | 1280 | -* |
| 111 | Riboflavin dinucleotide | 1 | 4 |
| 112 |  | 5 | 1 |
| 113 |  | 10 | 0 |
| 114 |  | 20 | 0 |
| 115 |  | 40 | 0 |
| 116 |  | 80 | 0 |
| 117 |  | 160 | 0 |
| 118 |  | 320 | 0 |
| 119 |  | 640 | 0 |
| 120 |  | 1280 | -* |
| 121 | Methylene blue | 1 | 7 |
| 122 |  | 5 | 3 |
| 123 |  | 10 | 1 |
| 124 |  | 20 | 0 |
| 125 |  | 40 | 0 |
| 126 |  | 80 | 0 |
| 127 |  | 160 | 0 |
| 128 |  | 320 | 0 |
| 129 |  | 640 | 0 |
| 130 |  | 1280 | 2 |
| 131 | Toluidine Blue | 1 | 8 |
| 132 |  | 5 | 3 |
| 133 |  | 10 | 1 |

TABLE 4-continued

The dependence of the effectiveness of the inactivation of the Newcastle disease virus with an initial dose of 10 lg TCA50/ml

| № p/p | Photosensitizer | Concentration nM/L | lg TCA50/ml after treatment |
|---|---|---|---|
| 134 | | 20 | 0 |
| 135 | | 40 | 0 |
| 136 | | 80 | 0 |
| 137 | | 160 | 0 |
| 138 | | 320 | 0 |
| 139 | | 640 | 0 |
| 140 | | 1280 | 0 |
| 141 | Dimethylmethylene blue | 1 | 3 |
| 142 | | 5 | 1 |
| 143 | | 10 | 0 |
| 144 | | 20 | 0 |
| 145 | | 40 | 0 |
| 146 | | 80 | 0 |
| 147 | | 160 | 0 |
| 148 | | 320 | 0 |
| 149 | | 640 | 0 |
| 150 | | 1280 | 0 |
| 151 | Chlorophyll alpha | 1 | 5 |
| 152 | (on TWEEN-80) | 5 | 3 |
| 153 | | 10 | 1 |
| 154 | | 20 | 0 |
| 155 | | 40 | 0 |
| 156 | | 80 | 0 |
| 157 | | 160 | 0 |
| 158 | | 320 | 0 |
| 159 | | 640 | 0 |
| 160 | | 1280 | -* |
| 161 | Heme | 1 | 4 |
| 162 | | 5 | 1 |
| 163 | | 10 | 1 |
| 164 | | 20 | 0 |
| 165 | | 40 | 0 |
| 166 | | 80 | 0 |
| 167 | | 160 | 0 |
| 168 | | 320 | 0 |
| 169 | | 640 | 0 |
| 170 | | 1280 | -* |
| 171 | Cyanocobalamin | 1 | 7 |
| 172 | | 5 | 6 |
| 173 | | 10 | 5 |
| 174 | | 20 | 4 |
| 175 | | 40 | 4 |
| 176 | | 80 | 2 |
| 177 | | 160 | 1 |
| 178 | | 320 | 1 |
| 179 | | 640 | 0 |
| 180 | | 1280 | -* |

*- not tested due to the inability to achieve the target concentration

As per table 4, in the range of concentrations from 5 to 640 nM/L, most photoinactivators showed sufficient effectiveness to inactivate the Newcastle disease virus.

Then, covalent modification of the viral antigen was carried out with two to five modifiers in terms of protein, as shown in Example 1. A detailed description of the modification is given below.

As the initial viral vaccine antigens also can be used: viral capsid proteins, agglutinins. Before or after photoinactivation, such a viral antigen can be cut into fragments using proteases, including but not limited to trypsin, pepsin, proteinase-K, chymotrypsin, using synthetic proteases. As salts of divalent metals, water-soluble salts can be used both separately and in mixtures with each other, inclusive, but not excluding: magnesium, calcium, zinc, iron, copper, strontium, cobalt, nickel.

Instead of the whole virion, the following can be used: a viral protein, a mixture of viral proteins or viral antigens previously cut with proteases. The initial antigens can be viruses: influenza, hepatitis, herpes viruses, measles, rubella, HIV/AIDS, animal viral infections: Newcastle disease, infectious bursal disease of the bird, classical swine fever, African swine fever and any other diseases, therapy of multiple sclerosis (Table 5).

TABLE 5

Promising products and diseases from which we will be able to be protected:

| № p/p | Application area | A pathology where vaccination will be much more effective | New consumer qualities |
|---|---|---|---|
| 1. | Veterinary science | African swine fever | An increase to 99% of the degree of protection of the livestock from one or two vaccinations, a decrease in the death of animals during the vaccination process (live attenuated virus strains from vaccines still kill up to 10% of the livestock). Reducing the effect of the fall in the planned weight gain of animals during vaccination (during the propagation of vaccine strains, the animal becomes sick and refuses food. This is very important when growing broilers). Real protection against especially dangerous infections (Africans, Aujeszky, bird flu, dog and cat distemper), where vaccination efficiency is close to 40%, and in other animals the disease is weaker and a small part of them survives, while almost all of unvaccinated animals die). |
| 2. | | Auesqui's disease | |
| 3. | | Newcastle Disease | |
| 4. | | Rabbit Hemorrhagic Fever | |
| 5. | | Dog/cat distemper | |
| 6. | | Horse Encephalitis | |
| 7. | | Bird infectious laryngotracheitis | |
| 8. | | Rabies | |
| 9. | | Pasteurellosis | |
| 10. | | RSV virus | |
| 11. | | Parainfluenza type 3 | |
| 12. | | Infectious bursal disease | |
| 13. | | Bovine Infectious Rhinotracheitis | |
| 14. | | Foot and mouth disease | |
| 15. | | Adenoviruses | |
| 16. | | Dog enteritis virus | |
| 17. | | Coronavirus | |
| 18. | | Ornithosis | |
| 19. | | Salmonellosis | |
| 20. | | Cattle Nodular Dermatitis | |
| 21. | | Smallpox of sheep and goats | |
| 22. | | Bird flu | |
| 23. | | Anthrax | |
| 24. | Medicine | Herpes viruses of 1-2 types | Increasing the effectiveness of both as a treatment and also prevention of herpes |
| 25. | | Herpes Zoster | Prevention of severe complications associated with the use of a live vaccine. |
| 26. | | Epstein-Barr virus | There are no vaccines, it can be effective both in the prevention of mononucleosis and in the treatment of complications of this viral infection (atherosclerosis and cancer) |
| 27. | | Cytomegalovirus | No vaccines can be effective both in the prevention and in the complications of this viral infection (atherosclerosis and cancer) |
| 28. | | Herpes virus type 6 | No vaccines, offered first time |
| 29. | | Measles | Offered safe and effective replacement for live highly reactogenic vaccines. |
| 30. | | Rubella | |
| 31. | | Polio | |

Due to the partial modification of the antigen structure during the modification reaction, a huge number of various vaccine antigen derivatives with different immunogenicity and structure are formed, and accordingly, the immune system induces the synthesis of more monoclones in response to these new antigenic determinants. In addition, such a variety of new epitopes (hundreds of thousands or even millions) allows us to predictively protect the body from future nonexistent strains of the flu and mutant HIV/AIDS viruses.

TABLE 6

The dependence of the effectiveness of the inactivation of the Newcastle disease virus. All depends on the wavelength of electromagnetic radiation at an initial dose of 10 lg CFU/ml

| № p/p | Photosensitizer | Wavelength nm | lg TCD50/ ml after treatment |
|---|---|---|---|
| 75. | Riboflavin | 180 | 0 |
| 76. | | 220 | 1 |
| 77. | | 260 | 1 |
| 78. | | 320 | 0 |
| 79. | | 360 | 0 |
| 80. | | 400 | 0 |
| 81. | | 440 | 0 |
| 82. | | 480 | 0 |
| 83. | | 520 | 9 |
| 84. | | 560 | 9 |
| 85. | | 600 | 9 |
| 86. | | 640 | 9 |
| 87. | | 680 | 7 |
| 88. | | 720 | 6 |
| 89. | Methylene blue | 180 | 10 |
| 90. | | 220 | 10 |
| 91. | | 260 | 9 |
| 92. | | 320 | 9 |
| 93. | | 360 | 9 |
| 94. | | 400 | 9 |
| 95. | | 440 | 8 |
| 96. | | 480 | 7 |
| 97. | | 520 | 4 |
| 98. | | 560 | 3 |
| 99. | | 600 | 2 |
| 100 | | 640 | 0 |
| 101 | | 680 | 0 |
| 102 | | 720 | 0 |
| 103 | Chlorophyll alpha | 180 | 8 |
| 104 | (on TWEEN-80) | 220 | 9 |
| 105 | | 260 | 10 |
| 106 | | 320 | 10 |
| 107 | | 360 | 10 |
| 108 | | 400 | 9 |
| 109 | | 440 | 9 |
| 110 | | 480 | 6 |
| 111 | | 520 | 7 |
| 112 | | 560 | 0 |
| 113 | | 600 | 0 |
| 114 | | 640 | 4 |
| 115 | | 680 | 5 |
| 116 | | 720 | 9 |

As on table 6, the highest inactivation efficiency for derivatives of flavins (riboflavin) is observed in the ultraviolet region of the spectrum (180-390 nm), for phenothiazines and porphyrins in the red region of the visible spectrum (500-700 nm)

Double Covalent Modification of Viral Antigen to Increase Vaccine Immunogenicity.

According to the number of virions, the viral suspension responded to 10 lg TCD50/ml; then 0.1 ml of the suspension was diluted 100 times with 0.9% sodium chloride solution and the concentration of surface proteins was established using the Biuret method and in the complexation reaction with the bromophenol blue method of Flores.

In terms of protein, a double covalent modification reaction was carried out by adding to the suspension inactivated virions, crushed to succinic and maleic anhydride powder in an amount of 0.1 to 10% of the specified amount of protein. Instead of succinic and maleic anhydrides, other combinations of modifiers can be used including, but not limited to: anhydrides of carboxylic and polycarboxylic acids, halides of carboxylic and polycarboxylic acids.

As a result of the modification reaction, 8 samples with different degrees of acylation were obtained: 1%, 3%, 5%, 7%, 9%, 11%, 13%, 15%. Exceeding 15% completely deprives immunogenicity of modified antigens, therefore derivatives with degrees of modification greater than 15% were not considered advisable to receive and use in the future. Viral antigen (virion) with varying degrees of modification was further used to establish its immunogenicity. A soluble peptide viral antigen was also obtained by trypsinization of the virion and isolation of a protein fraction with a molecular weight of about 18 kDa (NewcastleCastle virion surface receptor proteins) by gel filtration, and then derivatives with such degrees of modification were obtained: 1%, 3%, 5%, 7%, 9%, 11%, 13%, 15%.

Virus antigens can be modified, but not limited to alkylation, acylation with modifiers such as carboxylic and polycarboxylic acid anhydrides, halogenated carboxylic and polycarboxylic acids, either individually or in a different combination or mixture.

Inactivated and modified samples were taken for immunization of animals: virion antigen (VA) and surface virion antigen (SA).

The level of antibodies was established by two methods: a hemaglutination reaction and a method of fluorescent antibodies. Three animals from each group were left alive for up to 15 days, decapitated with chloroform and serum was obtained, where the level of specific antibodies was also established by the above methods. To implement this, a test system for the direct hemagglutination reaction was prepared, which was carried out in 96-well round-bottom immunological plates, to which 0.02 ml of a 0.1% suspension of thermostated ram erythrocytes and 0.02 ml of a suspension of thermally inactivated Newcastle disease virions were added at a concentration of 10 lg TCD50/ml.

Antibody levels were determined by serial ten-fold (but two-fold) dilutions of the blood sera of mice, which were added in an amount of 0.02 ml to the wells of the plates. The presence of agglutinates testified to the formation of immune complexes. As controls, we used normal human immunoglobulin (the antiviral antibody titer ranged from 0 to (1:10) according to the Analytic Normative Documentation) and the blood serum of unvaccinated mice (titer from 0 to 1:10).

The results of studies of samples of vaccine antigens on the example of the virions of the Newcastle disease virus are shown in table 7.

TABLE 7

Dependence of the immunogenicity of binary covalently modified antigens of the Newcastle disease virus from the degree of modification using whole virions and a single surface protein as an example.

| № p/p | Antigen | The degree of modification, % | Induced titer of neutralizing antibodies (1:X), X * |
|---|---|---|---|
| 1. | VA | 0 | 10 |
| 2. | | 1 | 100 |
| 3. | | 3 | 5000 |
| 4. | | 5 | 10000 |
| 5. | | 7 | 5000 |
| 6. | | 9 | 2500 |
| 7. | | 11 | 75 |
| 8. | | 13 | 75 |
| 9. | | 15 | 25 |
| 10. | SA | 0 | 10 |
| 11. | | 1 | 50 |
| 12. | | 3 | 100 |
| 13. | | 5 | 10000 |
| 14. | | 7 | 100 |
| 15. | | 9 | 50 |
| 16. | | 11 | 25 |
| 17. | | 13 | 25 |
| 18. | | 15 | — |

$P < 0.05$; * - differences from control are statistically significant

As can be seen from table 7, the highest antibody titers are induced by a virion covalently modified antigen. At degrees of modification from 3 to 7, the titer exceeded the original native (1:10) for unmodified antigens. The degree of protection of a single surface virion antigen was lower than for the whole virion, but it was 2 orders of magnitude higher than the protective level (1:10 for unmodified viral antigens).

Therefore, the bivalent modification after inactivation by the photodynamic method allows to increase the immunogenicity of antigens by several orders of magnitude based on the neutralization of unmodified corpuscles. In the prototype, it was possible to increase the immunogenicity of the antigen only to a titer of 1:5000. The obtained modified antigen can be sorbed by standard methods known to an ordinary person skilled in the art on an iron hydroxide hydrosol to further prolong the effects of the vaccine.

Determination of Reactogenicity and Allergenicity of Vaccines Based on Antigens of the Newcastle Disease Virus.

The studies on the reactogenicity and allergenicity of the solution of each of the vaccine antigens were carried out on healthy guinea pigs weighing 300-400 g of 3 animals in the control and experimental groups. In experimental animals, fur was depilated on the sides. To determine the reactogenicity, a solution of the corresponding antigen was injected intracutaneously on one side of the body in a volume of 0.2 ml. To determine allergenicity, test animals were injected intracutaneously with a triple vaccine antigen in a volume of 0.2 ml with an interval of 14 days, and 14 days after the last injection, guinea pigs were injected with a subcutaneous vaccine antigen in a volume of 0.2 ml.

The animals of the control group were injected with saline. The place of administration of the vaccine antigen was monitored for the occurrence of local reactions in the first 5 minutes and every 2 hours for 24 hours. Redness of the skin at the injection site in the area of not more than 5 mm is allowed. As a result of the studies, it was found that none of the photoinactivated bivalently modified viral antigens with degrees of modification from 3 to 15% showed reactogenicity and allergenicity. Among unmodified virus antigens, similar antigens also did not show allergenicity after repeated injections.

The Main Advantages of the Vaccines that we Offer are:

1. An increase in immunogenicity by 3 orders of magnitude compared to existing vaccines
2. Extension of the spectrum of action on low-immunogenic or non-immunogenic antigens (herpes viruses, human encephalitis viruses, RSV—virus, rotaviruses, coronaviruses, paramyxoviruses, Mycobacterium tuberculosis, african swine fever virus, Auezky disease, classical swine fever)
3. A decrease of 2-3 orders of allergenicity and reactogenicity of vaccines by reducing the effective vaccinating dose of antigen in the vaccine with the same effectiveness and immunogenicity.
4. Cheaper vaccine production technology by reducing the number of stages of production associated with current vaccine need to clean from formalin residues and the need to add special adjuvants (substances that increase the overall immunogenicity of vaccines such as aluminum hydroxide).
5. Extension of vaccination efficiency to prospective (not yet existing) antigens of influenza and other viral infections with a highly variable genome and antigenicity due to an increase in the number of available epitopes of antigens. This will protect not only from one strain of influenza, but also from non-existing, upcoming variants of the virus strains.
6. The ability to obtain ultra-polyvalent vaccines containing 20 or more different antigens in a mixture with the same effectiveness as a single vaccine.
7. The possibility of replacing ALL vaccines based on live attenuated microorganisms and viruses with inactivated and low reactivity, but with the same effectiveness and immunogenicity.

LIST OF REFERENCES

1. Robbins, J. B., R. Schneerson, and S. C. Szu. 1995. Perspective: hypothesis: serum IgG antibody is sufficient to confer protection against infectious disease by inactivating the inoculum. J. Infect. Dis. 171:1378-1398.
2. Del Val, M., H. J. Schlicht, H. Volkmer, M. Messerle, M. J. Reddehase, and U. H. Koszinowski. 1991. Protection against lethal cytomegalovirus infection by a recombinant vaccine containing a single nonameric T-cell epitope. J. Virol. 65:3641-3646
3. Larsen, D. L., A. Karasin, and C. W. Olsen. 2001 Immunization of pigs against influenza virus infection by DNA vaccine priming followed by killed-virus vaccine boosting. Vaccine 19:2842-2853
4. Cicin-Sain, L., Brune, W., Bubic, I., Jonjic, S., Koszinowski, U. H. (2003). Vaccination of Mice with Bacteria Carrying a Cloned Herpesvirus Genome Reconstituted In Vivo. J. Virol. 77: 8249-8255
5. Levin S A, Dushoff J, Plotkin J B. Evolution and persistence of influenza A and other diseases. Math Biosci. 2004 March-April; 188:17-28.
6. Terregino C, Toffan A, Beato M S, De Nardi R, Drago A, Capua I. Conventional H5N9 vaccine suppresses shedding in specific-pathogen-free birds challenged with HPAI H5N1 A/chicken/Yamaguchi/7/2004. Avian Dis. 2007 March; 51(1 Suppl):495-7.
7. Medvedeva M N, Petrov N A, Vasilenko S K, Simanovskaia V K, Golubev D B. The characteristics of the hemagglutinin from persistent variants of the influenza virus A/Victoria/35/72 (H3N2). Vopr Virusol. 1990 September-October; 35(5):374-6.
8. Aronsson F, Robertson B, Ljunggren H G, Kristensson K. Invasion and persistence of the neuroadapted influenza virus A/WSN/33 in the mouse olfactory system. Viral Immunol. 2003; 16(3):415-23.
9. Cox M M. Vaccines in development against avian influenza. Minerva Med. 2007 April; 98(2):145-53.
10. Gronvall G K, Borio L L. Removing barriers to global pandemic influenza vaccination. Biosecur Bioterror. 2006; 4(2):168-75.
11. Martynov A. V., Babych E. M., Smelyanskaya M. V. Increase of vaccines adjuvanticity by succinylation of vaccine antigen//Rejuvenation Research.—August 2005, Vol. 8, No. 1:P. 14-17 (Poster of Conference)
12. Taubenberger J K, Morens D M, Fauci A S. The next influenza pandemic: can it be predicted? JAMA. 2007 May 9; 297(18):2025-7.
13. Vardavas R, Breban R, Blower S. Can influenza epidemics be prevented by voluntary vaccination? PLoS Comput Biol. 2007 May 4; 3(5):e85.
14. Mintz P D (2011) Cesium cessation? An advantage of pathogen reduction treatments. Transfusion 51(7): 1369-1376.
15. Castrillo S M, Schneider V, Gathof B S (2009) Functional characteristics of apheresis-derived platelets treated with ultraviolet light combined with either amotosalen-HCI(S-59) or riboflavin (vitamin B2) for pathogen-reduction. Vox Sang 97(1): 26-33.

16. Reikvam H, Marschner S, Apelseth T O, Goodrich R, Hervig T (2010) The Mirasol Pathogen Reduction Technology system and quality of platelets stored in platelet additive solution. Blood Transfus 8(3): 186-192.
17. Webert K E, Cserti C M, Hannom J, Lin Y, Pavenski K, et al. (2008) Proceedings of a consensus coference: pathogen inactivation making decision about new technologies. Transfus Med Rev 22(1): 1-34.
18. Marschner S, Fast L D, Baldwin W M, Slichter S J, Goodrich R P (2010) White blood cell inactivation after treatment with riboflavin and ultraviolet light. Transfusion 50(11): 2489-2498.
19. Solheim B G (2008) Pathogen reduction of blood components. Transfus Apher Sci 39(1): 75-82.
20. Mandels, G. (1950). The photoinactivation of enzymes by riboflavin. *Plant Physiology,* 25(4), 763-766.
21. Eubanks, L. M., Dickerson, T. J., & Janda, K. D. (2005). Vitamin B2-mediated cellular photoinhibition of botulinum neurotoxin A. FEBS Letters, 579(24), 5361-5364. http://doi.org/10.1016/j.febslet.2005.08.072
22. US Application US20120195925A1

The invention claimed is:

1. A vaccine, comprising an antigen and an adjuvant, wherein the vaccine antigen is inactivated by ultraviolet and visible light in the presence of a solution of photosensitizer and divalent metal salts, and then the vaccine antigen is covalently modified simultaneously with at least two modifying agents at amino groups and alcohol hydroxyl groups that are accessible for modification, wherein the at least two modifying agents are employed at a concentration of 0.01-10.0% by mass relative to the antigen, and the adjuvant contains an iron hydroxide hydrosol.

2. The vaccine according to claim 1, wherein the photosensitizer is a riboflavin, a riboflavin mononucleotide, or a riboflavin dinucleotide.

3. The vaccine according to claim 1, wherein the photosensitizer is methylene blue, toluidine blue, or dimethylmethylene blue.

4. The vaccine according to claim 1, wherein the photosensitizer is a chlorophyll, a hematoporphyrin, or a cobalamin.

5. The vaccine according to claim 1, wherein the photosensitizer includes one or more of a riboflavin, a riboflavin mononucleotide, a riboflavin dinucleotide, methylene blue, toluidine blue, dimethylmethylene blue, a chlorophyll, a hematoporphyrin, and a cobalamin.

6. The vaccine according to claim 1, wherein the vaccine antigen is a corpuscle of a living microorganism.

7. The vaccine according to claim 1, wherein the vaccine antigen is a phagolysate of the microorganism.

8. The vaccine according to claim 1, wherein the vaccine antigen is a virion.

9. The vaccine according to claim 1, wherein the vaccine antigen is a microbial exotoxin.

10. The vaccine according to claim 1, wherein the vaccine antigen is a microbial endotoxin.

11. The vaccine according to claim 1, wherein the vaccine antigen is a microbial glycoprotein.

12. The vaccine according to claim 1, wherein the vaccine antigen is a mixture of microbial glycoproteins.

13. The vaccine according to claim 1, wherein the vaccine antigen is a microbial peptide.

14. The vaccine according to claim 1, wherein the vaccine antigen is a mixture of microbial peptides.

15. The vaccine according to claim 1, wherein the vaccine antigen is a microbial polysaccharide.

16. The vaccine according to claim 1, wherein the vaccine antigen is a mixture of microbial polysaccharides.

17. The vaccine according to claim 1, wherein the vaccine antigen is a microbial lipopolysaccharide.

18. The vaccine according to claim 1, wherein the vaccine antigen is a mixture of microbial lipopolysaccharides.

19. The vaccine according to claim 1, wherein the vaccine antigen is a whole virion.

20. The vaccine according to claim 1, wherein the vaccine antigen is a viral protein.

21. The vaccine according to claim 1, wherein the vaccine antigen is a mixture of viral proteins.

22. The vaccine according to claim 1, wherein the vaccine antigen is a mixture of an antigen protein pre-cut into fragments using proteases, including, but not limited to trypsin, pepsin, proteinase-K, chymotrypsin.

23. The vaccine according to claim 1, wherein the vaccine antigen is a mixture of an antigen protein, previously cut into fragments using synthetic proteases.

24. The vaccine according to claim 1, wherein the salts of divalent metals are separately mixed with each other as water-soluble salts, and include one or more of magnesium, calcium, zinc, iron, copper, strontium, cobalt, and nickel salts.

25. The vaccine according to claim 1, wherein the amino groups and alcohol hydroxyl groups that are accessible for covalent modification are present on lysine and histidine residues of a protein component of the antigen, the covalent modification is acylation and the at least two modifying agents include carboxylic and polycarboxylic acid anhydrides.

26. The vaccine according to claim 1, wherein the amino groups and alcohol hydroxyl groups that are accessible for covalent modification are present on lysine and histidine residues of a protein component of the antigen, the covalent modification is alkylation and the at least two modifying agents include halogen-substituted carboxylic and polycarboxylic acids.

27. The vaccine according to claim 1, wherein the amino groups and alcohol hydroxyl groups that are accessible for covalent modification are present on lysine and histidine residues of a protein component of the antigen, the covalent modification includes both acylation and alkylation and the at least two modifying agents include anhydrides of carboxylic and polycarboxylic acids and halogen-substituted carboxylic and polycarboxylic acids, respectively.

* * * * *